United States Patent
Vanderbist et al.

(10) Patent No.: US 7,090,870 B1
(45) Date of Patent: Aug. 15, 2006

(54) DRY POWER INHALER EXCIPIENT, PROCESS FOR ITS PREPARATION AND PHARMACEUTICAL COMPOSITIONS CONTAINING IT

(76) Inventors: Francis Vanderbist, Avenue des Jardinets 18, B-1170 Brussels (BE); Philippe Baudier, Avenue Blucher 10, B-1410 Waterloo (BE); Paul Maes, c/o Biovail Technologies, Ltd., 3701 Concorde Pkwy., Chantilly, VA (US) 20151

(*) Notice: Subject to any disclaimer, the term of this patent is extended or adjusted under 35 U.S.C. 154(b) by 0 days.

(21) Appl. No.: 09/424,247

(22) PCT Filed: May 7, 1998

(86) PCT No.: PCT/BE98/00064

§ 371 (c)(1),
(2), (4) Date: Oct. 30, 2002

(87) PCT Pub. No.: WO98/50015

PCT Pub. Date: Nov. 12, 1998

(30) Foreign Application Priority Data

May 7, 1997 (EP) .................................. 97870065

(51) Int. Cl.
*A61K 33/08* (2006.01)
(52) U.S. Cl. ...................................... 424/689
(58) Field of Classification Search ................ 424/240, 424/45, 689
See application file for complete search history.

(56) References Cited

U.S. PATENT DOCUMENTS

| | | | |
|---|---|---|---|
| 3,802,914 A | | 4/1974 | Nezbed |
| 4,199,578 A | * | 4/1980 | Stevenson .................... 514/171 |
| 5,254,330 A | * | 10/1993 | Ganderton et al. ............ 424/46 |
| 5,376,386 A | * | 12/1994 | Ganderton et al. ......... 424/499 |
| 5,551,489 A | | 9/1996 | Trofast et al. |
| 5,591,419 A | * | 1/1997 | McManus et al. ........ 423/576.6 |
| 5,612,053 A | * | 3/1997 | Baichwal et al. ............ 424/440 |
| 6,129,905 A | * | 10/2000 | Cutie ........................... 424/45 |
| 6,284,287 B1 | * | 9/2001 | Sarlikiotis et al. ........... 424/689 |

FOREIGN PATENT DOCUMENTS

| | | |
|---|---|---|
| EP | 0 964675 | 5/1998 |
| WO | 91/11179 | 8/1991 |
| WO | 95/24889 | 9/1995 |
| WO | WO 98 50015 | 11/1998 |

OTHER PUBLICATIONS

Eur Respr. J., Jan. 1994, Canada, Tomkiewicz, R.P. et al.*
Pulm Pharmacol., Dec. 1995, Canada, Tomkiewicz, R.P. et al.*

* cited by examiner

*Primary Examiner*—Vickie Kim
(74) *Attorney, Agent, or Firm*—Merchant & Gould, P.C.; William E. Beaumont

(57) ABSTRACT

A pharmaceutical excipient useful in the formulation of dry powder inhaler compositions comprising a particulate roller-dried anhydrous β-lactose, said β-lactose particles having a size between 50 and 250 micrometers and a rugosity between 1.9 and 2.4, and the so formulated pharmaceutical compositions.

17 Claims, 3 Drawing Sheets

10 micrometers

1000 X 100 micrometers

100 X

Figure 1:
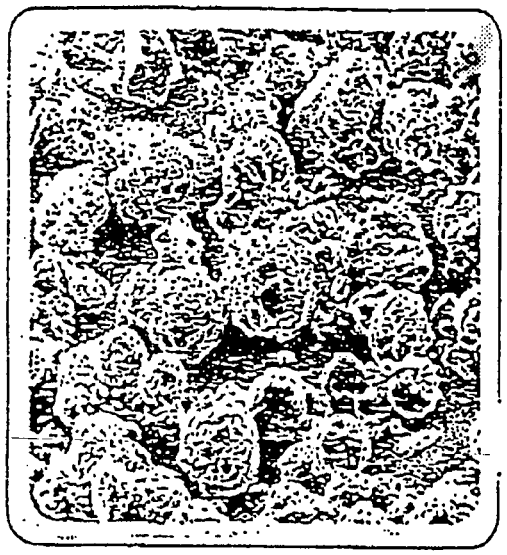
Figure 1:
Figure 1:
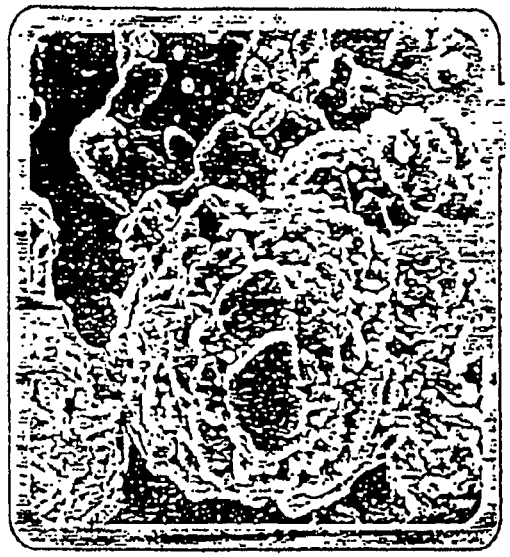
Figure 1:

DRY POWER INHALER EXCIPIENT, PROCESS FOR ITS PREPARATION AND PHARMACEUTICAL COMPOSITIONS CONTAINING IT

The present invention relates to a new pharmaceutical excipient which may be used in the formulation of dry powder inhaler compositions, to process for its preparation and to the so formulated pharmaceutical compositions.

The administration of active ingredients by inhalation has been used and recognised as a valuable technique for many years. Since the drug acts directly on the target organ, much smaller quantities of the active ingredient (when compared with oral route) may be used for obtaining the same activity, with at least the same duration of action and much fewer side effects due to the systemic absorption.

The three delivery systems available for allowing a pulmonary administration are nebulizers, pressurized metered dose inhalers (PMDIs) and dry powder inhalers (DPIs).

Nebulizers are effective but expensive, bulky and require a relatively long time of administration. As a result, they are mainly used in hospitals.

PMDIs were from far the most popular inhalation systems in the last two decades but present several disadvantages. They require a good coordination between actuation and inhalation what can be difficult for some patients. The respirable fraction that they allow to obtain is quite low (about 10%). And last but not least, their destructive effect on the ozone layer will led in a very close future to their complete removing. Now are appearing the first CFCs free PMDIs containing HFAs gases (hydrofluoroalkanes).

A variety of DPIs have been developed in the past few years and since DPIs rely on the inspiratory effort of the patient to produce a fine cloud of drug particles, the coordination problem associated with the use of MDIs does not apply. But, consequently, the quantity of the drug deposited in the lungs is dependent on the airflow. This dependence must be as low as possible for instance by improving the aerodynamic properties of the device and/or the quality of the formulation. There are two main kinds of DPIs (I) monodose DPIs in which the doses of active ingredient (mixed or not with an excipient) are preseparated by filling in individual gelatine capsules and (ii) multidose DPIs in which the drug (mixed or not with an excipient) is filled into a reservoir, the amount of drug delivered per actuation being controlled by a dosing chamber. A DPI's formulation typically presents a contradiction. Indeed, it is usually considered that for reaching the lungs, particle size must be smaller than 6 micrometers and to reach the deep regions of the lungs (bronchioles and alveoles), particle size must be smaller than 2 micrometers. Such micronized powders are very cohesive due to the numerous interparticles interactions occurring between them. This may cause an unreproducible filling of the gelatine capsules and/or incomplete output of the drug from the device. This is the reason why the active ingredient is either pelletized or mixed with a coarse excipient.

The lung deposition of a drug administered with a dry powder inhaler (DPI) is influenced by three kinds of parameters: the patient, the device and the formulation. Concerning the patient, the formulator must guarantee that the category of patients targeted will have a sufficient respiratory capacity to reach the wished amount of drug in the lung. Furthermore, the inhalation system has to be simple to use for allowing a good compliance from the patient. Nevertheless the patient must be duly trained to the inhalation technique. The choice of the inhalation device is of course important. The ideal device will be simple to use, portable, cheap, multidose, must allow to obtain a high respiratory fraction in a reproducible way, must possess a protecting system against an eventual overdosage, must be as low as possible dependent on the inhalation flow. It is clear that ideally each formulation must be optimized in function of the nature and the amount of active ingredient, the device and the category of patients targeted. The formulator has several parameters to play on for optimizing the formulation. The first condition for obtaining a high lung deposition is to possess a powder with a high percentage of respirable particles. The parameters influencing the lung deposition are the following: nature, size, shape and surface properties of the carrier particles, ratio between the active ingredient and the carrier, total amount in the capsule or in the dosing chamber, humidity and electrostatic forces. The physical characteristics of the excipient are from far the most important factor. Usually an inert water soluble, free flowing, coarse excipient is used as carrier. Most often, α-lactose is used but other mono- or disaccharides may be used. The principal interest of adding this excipient is to increase the flowability of the powder. Indeed, the micronized powders present a high number of interparticular interactions and are consequently very cohesive what can provoke a bad capsule filling in case of monodose devices, a bad output of the drug from the device due to the cohesiveness of the powder or a too low respiratory fraction due to the formation of agglomerates of active ingredients which are no more able to reach the lungs due to their too large dimensions. On the other hand, the bond between the carrier and the drug must be reversible during the inhalation for allowing the redispersion of the respirable active particles. This redispersion ideally occurs within the inhaler before the penetration in the mouth and is caused by the high turbulences created into the device by the patient's inhalation. Once the drug and the carrier are separated, their deposition in the different sites of the respiratory tract will depend on their size and mass and will be governed by inertial phenomenons. Ideally, excipient particles must deposite in the oro-pharyngeal region while the higher fraction possible of the drug must reach the deep lungs.

The most important parameters of for example α-lactose grains are the nature, the size, the flowability (Hausner ratio or angle of repose) and the rugosity which play a role in the strength of the bond between α-lactose and drug.

As it is well known, the surface characteristics of individual particles of the excipient may be modified by such conventional techniques as crystallization, spray drying and precipitation. For that purpose, patent application WO No. 91/11179 is directed to crystalline sugars such as α-lactose comprising particles having a rugosity of less than 1.75, which are useful in dry powder inhaler compositions. However, these crystalline excipients do not bind the active ingredient sufficiently strongly and generally give a mixture which is not stable and which segregates during handling and filling. On the contrary, the conventional excipients the rugosity of which is greater than 2.0, and particularly spray dried α-lactose monohydrate the rugosity of which is comprised between 2.4 and 2.8, may provoke a partially irreversible bond with the pharmaceutically active material with which it is formulated.

One of the aims of the present invention is consequently to overcome the above-mentioned drawbacks and to provide a novel form of particulate pharmaceutical excipient suitable for use in dry powder inhaler compositions, as polyvalent as possible allowing to obtain a high dose of the active ingredient in the lungs with a low variation between the inhalation device and the patients.

To this end, according to the invention, the excipient comprises a particulate roller-dried anhydrous β-lactose.

Advantageously, the roller-dried β-lactose particles have a size between 50 and 250 micrometers, preferably between 100 and 160 micrometers, and a rugosity comprised between 1.9 and 2.4.

It is also an object of the present invention to provide a process for preparing said roller-dried β-lactose excipient as well as the dry powder inhaler compositions obtained by mixing any suitable active ingredient or pharmacological agent with such particulate roller-dried β-lactose.

Further details and features of the invention will be evident from the detailed description given below of several particular embodiments of the invention.

As has already indicated above, the present invention mainly relates to the nature of the lactose particles used as excipient in the formulation of dry powder inhaler compositions and to the so obtained pharmaceutical compositions.

This lactose is an anhydrous roller-dried β-lactose, which is usually specifically used for direct compression and wet granulation thanks to its ability of being fragmented during compression so forming a high potential binding surface area. Such a form of β-lactose is for example obtained from DMV International under the trade designation Pharmatose DCL 21.

The structural formula of lactose is given hereinunder:

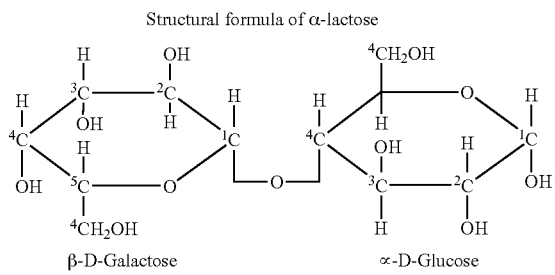

Structural formula of α-lactose

β-D-Galactose   α-D-Glucose

As shown hereinbelow, the differences between the two isomeric forms a and β rely on the configuration of the hydroxyl group on the glucose molecule;

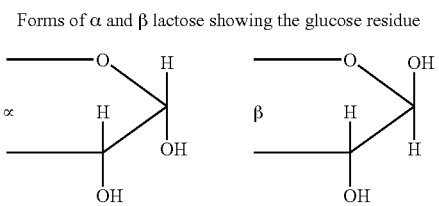

Forms of α and β lactose showing the glucose residue

Each form exist in a crystalline state α as a monohydrate and β anhydrous (plus an amorphous form which is a mixture of α and β). In aqueous solution α and β exist in equilibrium containing approximately 63% of the β form.

Following the conditions of crystallisation, it will be obtained less or more of the α or of the β form. For obtaining a maximum of β form, all the crystallization has to be done above 93.5° C.

The β-lactose used in the present invention is roller-dried. It is actually a lactose manufactured by the classical way including at least the following steps: evaporation-crystallisation-separation-washing-drying-sieving. But, once the lactose is produced in a powder form, it is redissolved in demineralised water, fed between two counterrotating drums, which are steam heated. The dried lactose is then screeped from the surface of the drums by knives. This particular type of lactose provides adequate surface properties for being used in dry powder inhaler formulations, e.g. able to form reversible bonds with pharmacological active ingredients. So this invention consist first of all in the use of a type of lactose, usually reserved for wet granulation and direct compression, for DPI formulations.

It must also be noted that the low water content of anhydrous β-lactose (<1%) compared to α-lactose monohydrate may be particularly advantageous when the active ingredient is highly hygroscopic and sensitive to moisture even if this molecule of water is an integrating part of the lactose molecule and is not easily released at low temperature. Examples of pharmacological agents which can be usefully mixed with the roller-dried β-lactose are the mucolytics, steroids, sympathomimetics, proteins, peptides and inhibitors of mediator's release. A specific example of mucolytic substance which may be used in the preparation of DPI compositions of the present invention is the L-lysine N-acetylcysteinate. L-lysine N-acetylcysteinate is a mucolytic and antioxidant drug presenting interesting properties in chronic lung diseases with hypertension like cystic fibrosis and chronic obstructive pulmonary disease. As is it well known, the active ingredient will be a particulate solid with a particle diameter preferably comprised between 0.5 and 6 micrometers in order to obtain a high lung deposition of it.

While not wishing to be bound by any theory, the fact that the roller-dried anhydrous β-lactose gives better results than the conventional α-lactose excipients, and more particularly than the spray-dried monohydrate α-lactose could be explained by more adequate surface properties for the roller-dried β-lactose which allows to obtain adequate binding forces between the drug and the excipient or carrier. These binding forces are essentially governed by the surface roughness (rugosity) of excipient particles. This rugosity is defined as the ratio between the surface area (derived from air permeability) to the theoretical external surface (assuming that all particles are spherical). Indeed the excipient must bind the active ingredient sufficiently strongly for allowing to obtain a stable and homogeneous mix which does not segregate during handling and filling. On the other hand, the link between drug and excipient may not be too strong in order that the individual drug particles may be redispersed during inhalation. Contrary to the above-mentioned patent application WO No. 91/11179 which describes the use of a recrystallized α-lactose of very low rugosity (1.75), the anhydrous roller-dried β-lactose used according to the present invention has a relatively high rugosity comprised between 1.9 and 2.4 This value is however inferior to this obtained with spray-dried α-lactose monohydrate which is comprised between 2.4 and 2.8. As already mentioned the higher rugosity of spray-dried α-lactose compared with roller-dried β-lactose may provoke a partially irreversible bond between lactose and drug, what may explain the lower lung deposition results of the spray-dried α-lactose monohydrate compared to the roller-dried anhydrous β-lactose, as it will be exemplified hereinafter.

As also indicated earlier the roller-dried β-lactose particles have preferably a size within the range of 50 to 250 micrometers and more preferably within the range of 100 to 160 micrometers.

The weight ratio of active ingredient to β-lactose excipient may vary depending upon the active ingredient used and in terms of its degree of activity. The optimum ratio will depend also upon the nature of the drug. In any way, it has been found that the use of weight ratios of active ingredient in relation to β-lactose excipient of from 0.1/100 to 50/100, provides satisfactory results.

The invention will now be illustrated in further detail by the following non-limiting Examples.

EXAMPLE 1

For proving its usefulness in dry powder formulations for inhalation, the roller-dried anhydrous β-lactose was compared with (i) a 325 mesh monohydrate crystalline α-lactose (which is the lactose usually used for DPI formulations), (ii) a coarser monohydrate crystalline α-lactose and (iii) a coarser spray-dried hydrous α-lactose. For this purpose, a formulation of 6 mg of L-lysine N-acetyl cysteinate (NAL) and 24 mg of the different lactose types were done and assessed in vitro on the 2 stages Twin Impinger at 60 l/min. The device used was the monodose Miat Inhaler Both the spray dried and the roller dried lactose were found to be superior in term of deposition than was the crystalline α-lactose probably because of more adequate surface properties. The results are shown in Table 1.

The fact that the granulometric range of 100–160 μm has given the best results in term of deposition may be explained by the differences in flowability (represented by the Hausner ratio) between the various size ranges of lactose tested as described in Table 3. The coarsest the lactose (in the range tested), the best is the flowability (and the lowest is the Hausner ratio).

TABLE 3

| Granulometric range of roller-dried anhydrous β-lactose (μm) | Hausner ratio |
| --- | --- |
| 125–160 | 1.14 |
| 90–125 | 1.16 |
| 75–90 | 1.33 |
| 63–75 | 1.49 |

Another advantage of using a coarse excipient in DPI formulations is that practically no lactose may reach the lungs in this case. Indeed, when the formulations using 63–90, 90–125 or 100–160 μm lactose are tested in vitro on the two stages Twin Impinger at 60 L/min, no lactose is

TABLE 1

In vitro deposition study (TI, 60 l/min.) with different lactose types using a 1:4 NAL/lactose mixture (30 mg of mixture/capsule). Three capsules/test (= 18 mg of NAL). Each result is the mean of 5 reproducible tests (n = 5).

|  | α-Lactose crystalline (325 mesh) | α-Lactose crystalline (63–100 μm) | Spray-dried α-lactose monohydrate (63–100 μm) | Roller-dried β-lactose anhydrous (63–100 μm) |
| --- | --- | --- | --- | --- |
| DEVICE (mg) | 6.3 ± 1.4 | 5.1 ± 1.2 | 4.9 ± 0.9 | 5.6 ± 1.2 |
| UPPER STAGE (mg) | 4.6 ± 1.2 | 5.8 ± 1.6 | 6.2 ± 1.4 | 5.8 ± 1.4 |
| LOWER STAGE (mg) | 3.2 ± 0.6 | 5.2 ± 1.1 | 5.5 ± 0.8 | 5.9 ± 0.7 |
| % RECOVERED | 78 ± 8 | 89 ± 9 | 92 ± 11 | 96.1 ± 12 |
| PULMONARY FRACTION (%) | 17 ± 3 | 29 ± 4 | 31 ± 6 | 33 ± 5 |

EXAMPLE 2

For founding the optimal granulometric range of lactose particles, three size (63–90 μm, 90—125 μm and 100–160 μm) ranges were assessed in vitro (TI) with both spray-dried and roller dried lactose. For this purpose, the various lactose were sieved twice successively on the appropriate sieves and the granulometric distribution was checked using the laser diffraction analysis (Mastersizer X, Malvern). The respiratory fraction increases with the excipient size. The roller-dried lactose of 100–160 μm was found to be the best excipient for NAL. The results are shown in Table 2.

detectable on the lower stage of the TI, while when conventional lactose of 325 mesh is tested in the same conditions, between 1 to 5% of lactose is able to reach the lower stage of the TI. This lung deposition of lactose may be responsible for some irritants effects of DPI formulations.

EXAMPLE 3

The last parameter to optimize is the ratio between drug and β-Lactose. Mixtures of NAL/β-lactose were realized from 1:2 to 1:6 (higher dilutions were not realistic because the therapeutical lung dose of NAL could not be reached)

TABLE 2

Influence of the nature and the size of the lactose particles on the in vitro deposition of NAL (TI at 60 l/min.). The ratio NAL/lactose (1:4) was the same for each lactose tested and 30 mg of powder was filled into capsule. (1 capsule/test). Each result is the mean ± SD of 3 values (n = 3).

|  | Spray-dried α-lactose monohydrate | | | Roller-dried β-lactose anhydrous | | |
| --- | --- | --- | --- | --- | --- | --- |
|  | 63–100 μm | 90–125 μm | 100–160 μm | 63–100 μm | 90–125 μm | 100–160 μm |
| DEVICE (mg) | 1.4 ± 0.4 | 1.7 ± 0.4 | 1.6 ± 0.2 | 1.6 ± 0.3 | 1.7 ± 0.5 | 1.6 ± 0.6 |
| UPPER STAGE (mg) | 2.0 ± 0.6 | 1.8 ± 0.5 | 2.00 ± 0.7 | 1.9 ± 0.6 | 1.6 ± 0.3 | 1.4 ± 0.2 |
| LOWER STAGE (mg) | 1.7 ± 0.3 | 1.7 ± 0.3 | 1.7 ± 0.6 | 2.1 ± 0.5 | 2.3 ± 0.6 | 2.5 ± 0.4 |
| % RECOVERED | 85 ± 8 | 86 ± 7 | 88 ± 10 | 92 ± 5 | 94 ± 8 | 91 ± 8 |
| PULMONARY FRACTION (%) | 28 ± 4 | 28 ± 5 | 28 ± 3 | 35 ± 4 | 39 ± 2 | 42 ± 3 | and assessed on the 2 stages Twin impinger using 30 mg of powder for each mixture. Mixtures from 1:2 to 1:4 were found to give the best results. The mixture 1:4 is definitely considered as the best as it is the only one who allows to obtain a high respirable fraction with keeping an acceptable flowability. The results are indicated in Table 4.

TABLE 4

Influence of the ratio NAL/β-lactose on the in vitro deposition of NAL (TI, 60 l/min.).
For each mixture 30 mg of powder was filled into capsule and each result presented is the mean ± SD of 3 values (n = 3).
The lactose used was the roller-dried β-lactose anhydrous of 100–160 μm (1 capsule/test).

|  | NAL/lactose 1:2 | NAL/lactose 1:3 | NAL/lactose 1:4 | NAL/lactose 1:5 | NAL/lactose 1:6 |
| --- | --- | --- | --- | --- | --- |
| DEVICE (mg) | 3.4 ± 1.0 | 2.5 ± 0.4 | 1.7 ± 0.3 | 1.6 ± 0.5 | 1.1 ± 0.4 |
| UPPER STAGE (mg) | 2.6 ± 0.9 | 1.7 ± 0.4 | 1.5 ± 0.5 | 1.5 ± 0.3 | 1.1 ± 0.4 |
| LOWER STAGE (mg) | 3.3 ± 1.1 | 2.5 ± 0.6 | 2.1 ± 0.5 | 1.0 ± 0.2 | 0.9 ± 0.2 |
| % RECOVERED | 95 ± 9 | 89 ± 7 | 88 ± 6 | 81 ± 10 | 71 ± 8 |
| PULMONARY FRACTION (%) | 35 ± 6 | 33 ± 5 | 32 ± 4 | 19 ± 3 | 22 ± 5 |

Figure 2:
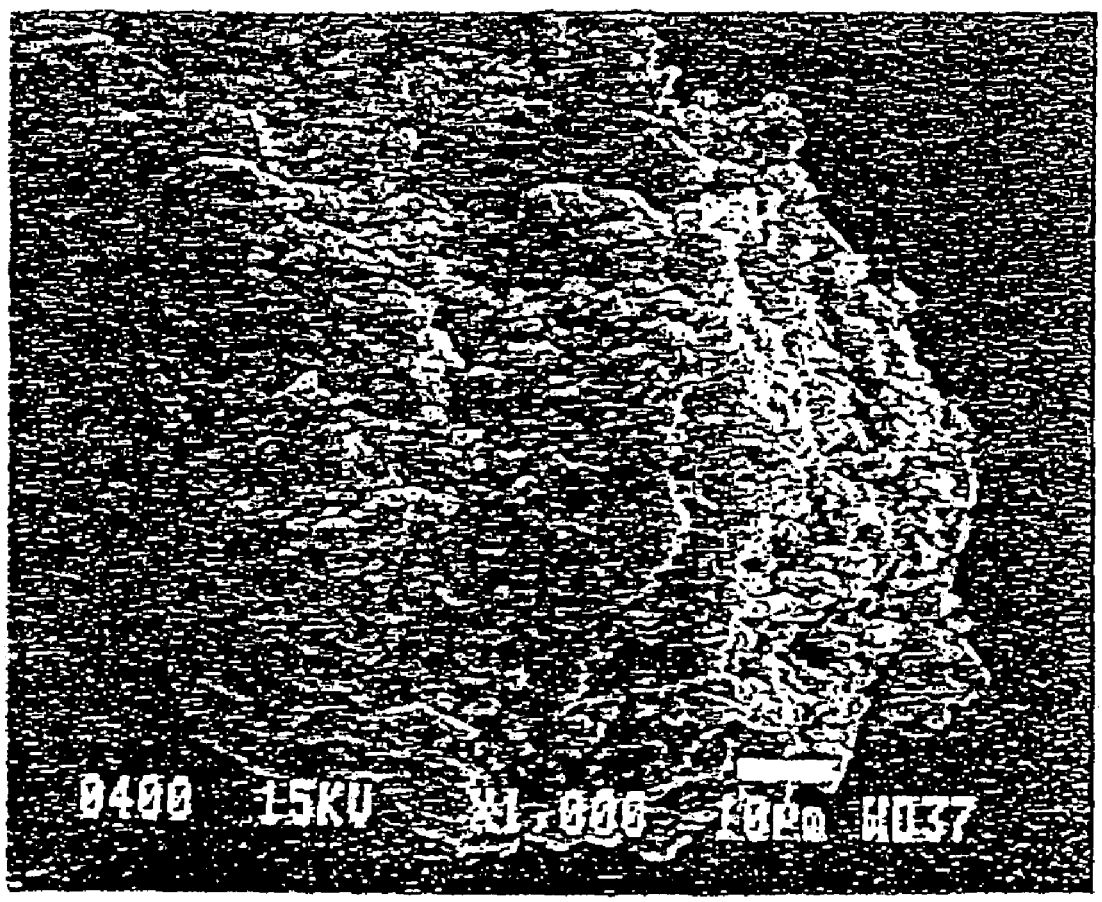
Figure 3:
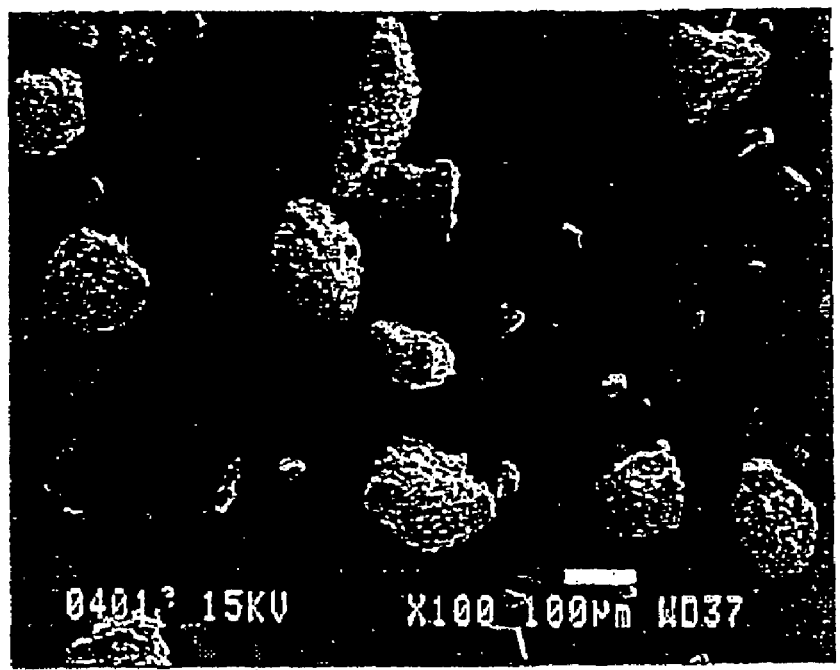
Figure 3:
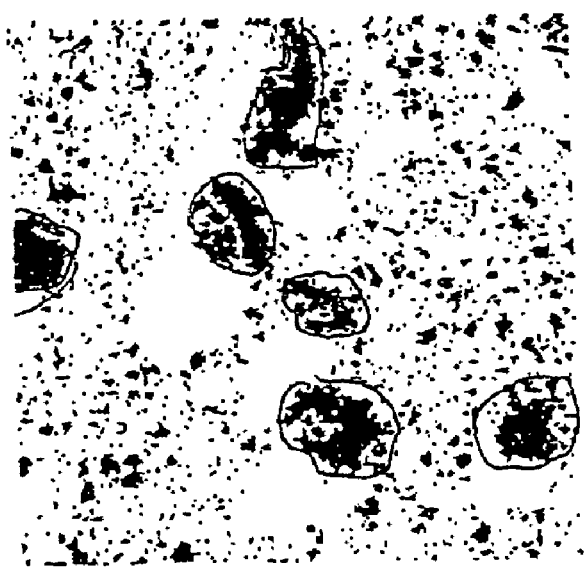

Electron micrographs of a selection of the above powders are shown in the accompanying Figures. In FIGS. 2 and 3, the magnification and an approximate scale is given.

FIG. 1 represents a picture taken by scanning electron microscopy (SEM) of a) the spray-dried α-lactose monohydrate and b) the roller-dried anhydrous β-lactose. It is well visible that there are significative differences between both types of lactose. The roller-dried β-lactose particles are less spherical and show a slightly smoother surface than the spray-dried lactose (what is a visual confirmation of the rugosity measurement).

FIG. 2 shows a picture taken by SEM of a grain of the roller-dried anhydrous β-lactose recovered by micronized particles of NAL.

FIG. 3 represents a wider view of the picture of FIG. 2. The mapping of the sulphur atom on this picture shows to what extent NAL is well fixed on the β-lactose grains.

An in vivo deposition study has been also realized on 6 volunteers to confirm the high respirable fraction obtained with the formulation. The mean lung deposition was superior to 30% and the lung penetration of the drug was good.

All the results described hereinabove were obtained by using the monodose Miat Inhaler. For proving that this kind of formulations is relatively polyvalent and not strictly developed for one device type, some tests were performed on a multidose DPI device. The formulation used was as follows:

NAL/roller dried anhydrous β-lactose (100—160 μm)1:4.

When tested on the TI at 60 l/min, the respirable fraction (in proportion of the nominal dose) obtained with this device was of 33±3% (n=10).

EXAMPLE 4 a) Budesonide

The therapeutical dose of the corticosteroid budesonide is very low. The nominal dose usually recommended is between 200 and 400 μg. The device used in the in vitro deposition tests with budesonide is the Miat multidose inhaler. It is completely different from the monodose device used for NAL as this last was a monodose capsule system whereas the multidose inhaler is a reservoir system working with a dosing chamber for administering the required dose of active ingredient.

Budesonide was assayed using the HPLC described in the European Pharmacopoeia $3^{rd}$ edition, 1997.

A mixture of budesonide with roller-dried anhydrous β-lactose (100–160 μm) was realized in the ratio 1:9. The dose emitted/puff is about 3 mg what means approximately 300 μg of budesonide/puff. When tested at 60 L/min, the respirable fraction eg the fraction <6.8 μm in comparison with the nominal dose was of 28.7±3.4%.

The same formulation has been tested in the same conditions with another multidose device: the Clickhaler® (ML Laboratories). The respirable fraction was of 27.9±4.5%.

b) Salbutamol

Salbutamol or albuterol is a β2-agonist widely used as bronchodilatator agent in asthma and copd. The therapeutical nominal dose by inhalation is of 100–200 μg. The device used is the Miat Multidose Inhaler.

Salbutamol was assayed using a spectrophotometric method. A mixture of salbutamol with roller-dried anhydrous β-lactose (100–160 μm) was realized in the ratio 1:19. The dose emitted/puff is about 3 mg what means approximately 150 μg of salbutamol/puff. When tested at 60 L/min, the respirable fraction eg the fraction <6.8 μm in comparison with the nominal dose was of 31.2±5.7%.

c) Sodium Cromoglycate (SCG)

Sodium cromoglycate is a prophylactic agent widely used in the chronic treatment of asthma. The therapeutical nominal dose usually used is of about 20 mg.

Sodium chromoglycate was assayed using a spectrophotometric method. A mixture of micronized SCG with roller-dried anhydrous β-lactose (100—160 μm) was realized in the ratio 1:2. The Monodose Miat Inhaler was for performing the in vitro deposition tests. 60 mg of the mix (corresponding to 20 mgf of SCG) has been put into No. 3 hard gelatin capsules.

The in vitro deposition (represented by the Mass Median Aerodynamic Diameter of MMAD) of the capsules, containing a mixture of micronized sodium cromoglycate fixed on roller-dried lactose DCL21 (100–160 μm) in the ratio 1:2, has been assessed at various airflow from 40 L/min up to 100 L/min and compared with the commercial Lomudal Spincaps® (Fisons). The apparatus used for assessing the deposition is the Multistage Liquid Impringer.

Table 5 hereinbelow gives the airflow influence on the MMAD and on the pulmonary fraction (PF %) for both formulations.

TABLE 5

| Airflow rate (L/min) | MMAD (μm) Roller-dried lactose | MMAD (μm) Lomudal Spincaps | PF % Roller-dried lactose | PF % Lomudal Spincaps |
| --- | --- | --- | --- | --- |
| 40 | 2.63 | 3.09 | 30.86 | 7.61 |
| 60 | 2.25 | 2.31 | 32.30 | 14.45 |
| 80 | 2.25 | 1.98 | 29.30 | 19.21 |
| 100 | 2.14 | 1.69 | 25.73 | 27.88 |

The very low dependence to the airflow presented by the formulation using roller-dried lactose guarantees that the lung deposition of SCG will be approximately the same for mild, moderately and severely ill patients (25 to 30%) while the situation is completely different with Lomudal Spincaps. Indeed, this kind of formulation gives a lung deposition of SCG 4 times superior when teted at 100 L/min in comparison to the test at 40 L/min corresponding to a very high intra and inter subject variation. This illustrates another potential advantage of the DPI formulation using roller-dried β-anhydrous lactose.

The foregoing is merely illustrative of the invention and is not intended to limit it to the disclosed excipients, methods and compositions. Many variations and changes which are obvious to one skilled in the art are intended to be within the scope and nature of the invention which are defined in the appended claims.

The invention claimed is:

1. A dry powder inhaler pharmaceutical composition comprising a mixture of one or more particulate pharmaceutically active ingredients and a particulate roller-dried anhydrous β-lactose excipient, said excipient having a particle size comprised between 50 and 250 μm, and a rugosity comprised between 1.9 and 2.4.

2. The composition of claim 1, in which the particulate roller-dried anhydrous β-lactose excipient has a particle size comprised between 100 and 160 μm.

3. The composition of claim 1, in which the particulate roller-dried anhydrous β-lactose excipient has a particle size comprised between 90 and 250 μm.

4. The composition of claim 1, in which the particulate roller-dried anhydrous β-lactose excipient is prepared from a lactose solution in demineralized water fed between two counter-rotating drums, which are steam-heated, and after drying scraped from the surface of the drums by knives.

5. The composition of claim 1, in which the particulate pharmaceutically active ingredients are a particulate solid with a particle diameter between 0.5 and 6 μm.

6. The composition of claim 1, in which the particulate pharmaceutically active ingredients are selected from the group consisting of mucolytics, steroids, sympathomimetics, proteins, peptides, inhibitors of mediators release and mixtures thereof.

7. The composition of claim 6, in which the composition comprises a mucolytic agent, which is L-lysine N-acetylcysteinate, as the pharmaceutically active ingredient.

8. The composition of claim 1, which comprises a mixture of particulate L-lysine N-acetylcysteinate and roller-dried anhydrous β-lactose excipient, said excipient being constituted by particles of 100 to 160 μm in size.

9. The composition of claim 7, in which the weight ratio of particulate L-lysine N-acetylcysteinate in relation to the particulate roller-dried anhydrous β-lactose excipient is between 1:2 to 1:6.

10. The composition of claim 3, in which the ratio of active ingredients/excipient is 1:4.

11. The composition of claim 1, wherein said pharmaceutically active ingredient is budesonide.

12. The composition of claim 1, wherein said pharmaceutically-active ingredient is salbutamol.

13. The composition of claim 1, wherein said pharmaceutically-active ingredient is sodium cromoglycate.

14. The composition of claim 9, wherein said weight ratio is 1:2 to 1:4.

15. A process for the preparation of a dry powder inhaler pharmaceutical composition comprising a mixture of a particulate pharmaceutically-active ingredient and a particulate roller-dried anhydrous β-lactose lactose excipient, which comprises a step of mixing a dry particulate pharmaceutical active ingredient with a particulate roller-dried anhydrous β-lactose excipient.

16. The process of claim 15, wherein the particulate roller-dried anhydrous β-lactose excipient has particle size comprised between 50 and 250 μm.

17. The composition of claim 1, having a ratio of active ingredients/excipient of from about 0.1/100 to about 50/100.

* * * * *